(12) United States Patent
Kneller et al.

(10) Patent No.: US 12,226,383 B1
(45) Date of Patent: Feb. 18, 2025

(54) COMPOSITIONS CONTAINING SHORT-CHAIN FATTY ACID, METHODS OF USE, AND METHODS OF MAKING THEREOF

(71) Applicant: Velocity Life Sciences, LLC, Port Jefferson, NY (US)

(72) Inventors: Bruce W. Kneller, Howell, NJ (US); Brandon S. Sojka, Port Jefferson, NY (US); Timothy N. Ziegenfuss, Chardon, OH (US)

(73) Assignee: Velocity Life Sciences, LLC, Port Jefferson, NY (US)

( * ) Notice: Subject to any disclaimer, the term of this patent is extended or adjusted under 35 U.S.C. 154(b) by 0 days.

(21) Appl. No.: 18/651,454

(22) Filed: Apr. 30, 2024

(51) Int. Cl.
*A61K 31/195* (2006.01)
*A61K 9/00* (2006.01)

(52) U.S. Cl.
CPC .......... *A61K 31/195* (2013.01); *A61K 9/0056* (2013.01); *A61K 9/0095* (2013.01)

(58) Field of Classification Search
CPC ............................ A61K 31/195; A61K 9/0056
See application file for complete search history.

(56) References Cited

U.S. PATENT DOCUMENTS

| 3,015,567 A | 1/1962 | Hause et al. |
| 3,024,272 A | 3/1962 | Hyson et al. |
| 2022/0142978 A1* | 5/2022 | Arzumanyan .......... A61P 37/08 |

FOREIGN PATENT DOCUMENTS

| CA | 1 209 037 | 8/1986 | |
| WO | WO-2023217675 A1 * | 11/2023 | ............. A23L 33/10 |

OTHER PUBLICATIONS

Gasiorowska et al. Effects of Microencapsulated Sodium Butyrate, Probiotics and Short Chain Fructooligosaccharides in Patients with Irritable Bowel Syndrome: A Study Protocol of a Randomized Double-Blind Placebo-Controlled Trial, J Clin Med; Nov. 2022, pp. 1-11. (Year: 2022).*
WO 2023217675 Machine translation (Year: 2023).*
Bartolomaeus, H. et al., "Short-chain fatty acid propionate protects from hypertensive cardiovascular damage", Circulation, vol. 139, pp. 1407-1421, (2019).
Bourassa, M.W. et al., "Butyrate, neuroepigenetics and the gut microbiome: Can a high fiber diet improve brain health?", Neuroscience Letters, vol. 625, pp. 56-63, (2016).
Byrne, C.S. et al., "The role of short chain fatty acids in appetite regulation and energy homeostasis", International Journal of Obesity, vol. 39, pp. 1331-1338, (2015).
Canfora, E.E. et al., "Short-chain fatty acids in control of body weight and insulin sensitivity", Nature Reviews, Endocrinology, vol. 11, pp. 577-591, (2015).
Conley, B.A. et al., "Phase I study of the orally administered butyrate prodrug, tributyrin, in patients with solid tumors", Clinical Cancer Research, vol. 4, pp. 629-634, (1998).
Edelman, M.J. et al., "Clinical and pharmacologic study of tributyrin: an oral butyrate prodrug", Cancer Chemotherapy and Pharmacology, vol. 51, pp. 439-444, (2003).
Egorin, M.J. et al., "Plasma pharmacokinetics of butyrate after intravenous administration of sodium butyrate or oral administration of tributyrin or sodium butyrate to mice and rats", Cancer Chemotherapy and pharmacology, vol. 51, pp. 439-444, (1998).
Faller, D.V. et al., "Short-term exposure to arginine butyrate, in combination with ganciclovir, is as effective as continuous exposure for virus-targeted therapy of EBV-positive lymphomas", Blood, vol. 114, No. 22, abstract 4754, (2009).
Guerron, A.D. et al., "Functional and molecular effects of arginine butyrate and prednisone on muscle and heart in the mdx mouse model of Duchenne muscular dystrophy", PLoS One, vol. 5, issue 6, e11220, pp. 1-12, (2010).
Hamer, H.M. et al., "Butyrate modulates oxidative stress in the colonic mucosa of healthy humans", Clinical Nutrition, vol. 28, pp. 88-93, (2009).
Kaye, D.M. et al., "Deficiency of prebiotic fiber and insufficient signaling through gut metabolite-sensing receptors leads to cardiovascular disease", Circulation, vol. 141, pp. 1393-1403, (2020).
Kim, S. et al., "Imbalance of gut microbiome and intestinal epithelial barrier dysfunction in patients with high blood pressure", Clinical Science, vol. 132, pp. 701-718, (2018).
Kuefer, R. et al., "Antagonistic effects of sodium butyrate and N-(4-Hydroxyphenyl)-retinamide on prostate cancer", Neoplasia, vol. 9, No. 3, pp. 246-253, (2007).
Bell, F.P., "The effect of fat-soluble xenobiotics on intestinal lipid, apoprotein, and lipoprotein synthesis and secretion", In Fat Absorption, Chapter 7, pp. 167-188, (2018).
Lupton, J.R., "Microbial degradation products influence colon cancer risk: the butyrate controversy", The Journal of Nutrition, vol. 134, No. 2, pp. 479-482, (2004).
Marques, F.Z. et al., "High-fiber diet and acetate supplementation change the gut microbiota and prevent the development of hypertension and heart failure in hypertensive mice", Circulation, vol. 135, pp. 964-977, (2017).
McGovern, M.M. et al., "Biochemical effect of intravenous arginine butyrate in x-linked adrenoleukodystrophy", The Journal of Pediatrics, vol. 142, No. 6, pp. 709-713. (2003).

(Continued)

*Primary Examiner* — San Ming R Hui
*Assistant Examiner* — Mikhail O'Donnel Robinson
(74) *Attorney, Agent, or Firm* — EVAN LAW GROUP LLC

(57) ABSTRACT

A food product comprises L-lysine butyrate. The food product does not contain gluten and is not a baked product. Alternatively, the product is an oral dosage form comprising 25 mg to 5.0 g L-lysine butyrate. The oral dosage form is a tablet, a capsule, or a sealed packet containing powder. In another alternative, orally administering L-lysine butyrate may be used to: supplementing butyrate, provide a nootropic effect, treat a condition, losing weight, improve cognition, induce or maintain ketosis, improve athletic performance, or treat or mitigate mild-to-moderate pain.

24 Claims, No Drawings

(56) References Cited

OTHER PUBLICATIONS

McMahon, L. et al., "A randomized phase II trial of arginine butyrate with standard local therapy in refractory sickle cell leg ulcers", British Journal of Haematology, vol. 151, pp. 516-524, (2010).

Merchak, A. et al., "Microbial metabolites and immune regulation: New targets for major depressive disorder", Brain, Behavior, & Immunity—Health, vol. 9, No. 100169, pp. 1-10. (2020).

Miller, S.J., "Cellular and physiological effects of short-chain fatty acids", Mini-Reviews in Medicinal Chemistry, vol. 4, pp. 839-845, (2004).

Miller, A.A. et al., "Clinical pharmacology of sodium butyrate in patients with acute leukemia", European Journal of Cancer and Clinical Oncology, vol. 23, No. 9, pp. 1283-1287, (1987).

Morrison, D.J. et al., "formation of short chain fatty acids by the gut microbiota and their impact on human metabolism", Gut Microbes, vol. 7, No. 3, pp. 189-200. (2016).

Moss, G.P. et al., "Glossary of class names of organic compounds and reactive intermediates based on structure", Pure and Applied Chemistry, vol. 67, No. 8/9, pp. 1307-1375, (1995).

Mueller, N.T. et al., "Effects of high-fiber diets enriched with carbohydrate, protein, or unsaturated fat on circulating short chain fatty acids: results from the omniheart randomized trail", The American Journal of Clinical Nutrition, vol. 111, No. 3, pp. 545-554, (2020).

Newmark, H.L. et al., "Butyrate and phenylacetate as differentiating agents: Practical problems and opportunities", Journal of Cellular Biochemistry, supplement 22, pp. 247-253, (1995).

Newmark, H.L. et al., "Butyrate as a differentiating agent: pharmacokinetics, analogues and current status". Cancer Letters, vol. 78, pp. 1-5, (1994).

Offermanns, S. et al., "International union of basic and clinical pharmacology, LXXXII: Nomenclature and classification of hydroxy-carboxylic acid receptors (GPR81, GPR109A, and GPR109B)", Pharmacological Reviews, vol. 63, pp. 269-290, (2011).

Perrine, S.P. et al., "A phase ½ trial of arginine butyrate and ganciclovir in patients with Epstein-Barr virus-associated lymphoid malignancies", Blood, vol. 109, No. 6, pp. 2571-2578, (2007).

National Institutes of Health, "Probiotics Fact Sheet for Health Professionals, Office of Dietary Supplements", National Institutes of Health, pp. 1-12, found at ods.od.nih.gov/factsheets/probiotics-healthprofessional, (2023).

Rhys-Jones, D. et al., "Microbial interventions to control and reduce blood pressure in Australia (MICRoBiA): rationale and design of a double-blinded randomized cross-over placebo controlled trial", Trials, vol. 22, pp. 1-7, (2021).

Xu, Q. et al., "The influence of bile salts on small intestinal motility in the guinea pig in vitro", Gastroenterology, vol. 103, pp. 29-35, (1992).

Seedorf, H. et al., "The genome of clostridium kluyveri, a strict anaerobe with unique metabolic features", PNAS, vol. 105, No. 6, pp. 2128-2133, (2008).

Serpe, L. et al., "Cholesteryl butyrate solid lipid nanoparticles as a butyric acid pro-drug: effects on cell proliferation, cell-cycle distribution and c-myc expression in human leukemic cells", Anti-Cancer Drigs, vol. 15, pp. 525-536, (2004).

Sher, G.D. et al., "Extended therapy with intravenous arginine butyrate in patients with β-hemoglobinopathies", The New England Journal of Medicine, vol. 332, No. 24, pp. 1606-1610, (1995).

Urbano, A. et al., "Arginine butyrate downregulates $p^{210}$ bcr-abl expression and induces apoptosis in chronic myelogenous leukemia cells", Leukemia, vol. 12, pp. 930-936, (1998).

Wong, J.M.W. et al., "Colonic health: Fermentation and short chain fatty acids", Journal of Clinical Gastroenterology, vol. 40, No. 3, pp. 235-243, (2006).

Coppola S. et al., "The protective role of butyrate against obesity and obesity-related diseases", Molecules, vol. 26, No. 3, 682, pp. 1-19, (2021).

Dziedzic, A. et al., "The power of psychobiotics in depression: A modern approach through the microbiota-gut-brain axis: A literature review", Nutrients, vol. 16, No. 7, 1054, pp. 1-24, (2024).

Muller, M. et al., "Circulating but not faecal short-chain fatty acids are related to insulin sensitivity, lipolysis and GLP-1 concentrations in humans", Scientific Reports, vol. 9, No. 1, pp. 1-9, (2019).

Chen, J.S. et al., "Short-chain fatty acid inhibitors of histone deacetylases: Promising anticancer therapeutics?", Current Cancer Drug Targets, vol. 3, No. 3, pp. 219-236, (2003).

Kantharaj, E. et al., "Histone deacetylase inhibitors as therapeutic agents for cancer therapy: Drug metabolism and pharmacokinetic properties", Drug Development—A case study based insight into modem strategies, pp. 101-111, (2011).

Kuksis, A., "Biochemistry of glycerolipids and formation of chylomicrons", Fat Digestion and Absorption, Chapter 7, pp. 119-181, (2000).

Pizzomo, J.E. et al., "Inflammatory bowel disease, in the Clinician's handbook of natural medicine E-Book", $3^{rd}$ Edition, Elsevier Health Sciences, pp. 547-564, (2015).

Scheppach, W. et al., "Effect of butyrate enemas on the colonic mucosa in distal ulcerative colitis", Gastroenterology, vol. 103, No. 1, pp. 51-56, (1992).

\* cited by examiner

COMPOSITIONS CONTAINING SHORT-CHAIN FATTY ACID, METHODS OF USE, AND METHODS OF MAKING THEREOF

BACKGROUND

Short-chain fatty acids (SCFAs) are fatty acids, carboxylic acids with an aliphatic chain, which are either saturated or unsaturated of two to six carbon atoms (Moss et al., 1995). SCFAs possess varying degrees of water solubility, distinguishing them from longer-chain, immiscible fatty acids. SCFAs are produced endogenously when dietary fiber is fermented in the colon (Canfora et al., 2015; Wong et al., 2006). Dietary macronutrient composition affects circulating SCFAs (Mueller et al., 2020). Derived from intestinal microbial fermentation of indigestible foods, the primary SCFAs in the human gut are acetic, propionic, and butyric acid. Highly fermentable fiber residues, such as those from resistant starch, oat bran, pectin, and guar and acacia gum, are transformed by colonic bacteria into SCFAs (Lupton, 2004; Morrison & Preston, 2016). SCFAs are primarily, but not exclusively, absorbed through the portal vein during lipid digestion (Kuksis, 2000).

SCFAs have diverse physiological roles in body functions. They can affect the production of lipids, energy and vitamins (Byrne et al., 2015). They can also affect appetite and cardiometabolic health (Mueller et al., 2020). Additionally, they may impact mental health and mood (Merchak & Gaultier, 2020). The three main SCFAs, acetate, propionate, and butyrate, were shown to lower blood pressure in a variety of experimental models (Bartolomaeus et al., 2019; Kaye et al., 2020; Kim et al., 2018; Marques et al., 2017) and clinical trials to determine their effect on hypertensive patients are underway (Rhys-Jones et al., 2021). In humans, butyric acid is one of two primary endogenous agonists of human hydroxycarboxylic acid receptor 2 (HCA2), a Gvio-coupled G protein-coupled receptor (Colletti et al., 2019; Offermanns et al., 2011). In studies on the treatment of ulcerative colitis, butyric acid was used in the form of enema at doses of 40 mmol/l to up to 100 mmol/l, which corresponds to 4.4-11 g/l; or sodium butyrate enemas at a dose of 8800 mg/I; for 200 ml enemas, this translates into 800-2200 mg per enema (Pizzorno et al., 2016; Hamer et al., 2009; Scheppach et al., 1992).

Butyric acid, also known under the systematic name butanoic acid, is a straight-chain alkyl carboxylic acid with the chemical formula $CH_3CH_2CH_2CO_2H$ and CAS number of 107-92-6, having a molar mass of about 88.11 g/mol. It is an oily, colorless liquid with a highly unpleasant odor and taste (reminiscent of human vomit). Humans can detect it in concentrations above 10 parts per million. The acid does not occur widely in nature, but its esters are widespread, such as in animal fat and plant oils, bovine milk, human breast milk, butter, parmesan cheese, body odor and vomit. Triglycerides of butyric acid compose 3-4% of butter. Salts and esters of butyric acid are known as butyrates or butanoates, and often also have an unpleasant odor and taste similar to that of the free acid. Butyrate is produced by several fermentation processes performed by obligate anaerobic bacteria (Seedorf et al., 2008). Butyric acid or butyrate is particularly important for colon health because it is the primary energy source for colonocytes (the epithelial cells of the colon) (Canfora et al., 2015).

Butyrate produced in the colon through microbial fermentation of dietary fiber is primarily absorbed and metabolized by colonocytes, and some is transported by the portal vein to the liver. However, some butyrate is absorbed in the distal colon, which is not connected to the portal vein, thereby allowing for the systemic distribution of butyrate to multiple organ systems through the circulatory system (Bourassa et al., 2016). Butyrate appears to play an essential role in human health, with a low fiber diet or depletion of butyrate producing bacteria in the gut being associate with numerous adverse health conditions. These include inflammation, allergic diseases, diabetes, vasculitis, ulcerative colitis, colorectal cancer, and addiction.

Compounds currently identified as useful for butyrate administration include butyric acid, sodium butyrate, and tributyrin (the tri-ester of butyric acid and glycerol). Potassium, magnesium, calcium and zinc butyrates have also been considered. L-arginine butyrate has been used as an aqueous solution for parenteral administration (Faller et al., 2009; Guerron et al., 2010; McGovern et al., 2003; McMahon et al., 2010; Perrine et al., 2006; Sher et al., 1995; Urbano et al., 1998).

U.S. Pat. No. 3,024,272 describes organic acid salts of basic amino acids as a preservative in baked goods, and to supplement L-lysine in such products which are known to be somewhat deficient in this amino acid. Synthesis of L-lysine propionate, L-lysine valerate (valeric acid being $CH_3(CH_2)_3COOH$) and L-arginine propionate are described, with L-lysine propionate being noted as somewhat hygroscopic. Lysine propionate, lysine butyrate and arginine propionate were tested in bread as a mold inhibitor, with the lysine butyrate being used in an amount of ¾ of one part per 60 parts flour. It is indicated that lysine propionate or an equivalent amount of a basic amino acid salt of propionic acid may be used to prevent mold growth in an amount of 0.01% to 2.5% based on the flour content of the product.

U.S. Pat. No. 3,015,567 describes a process for enriching the L-lysine content of foods containing wheat gluten which is known to be low in L-lysine. The authors note that a variety of L-lysine salts of various organic acids were prepared and found to lack any salty flavor, and therefore were not considered useful to enrich the content of the food products; these salts included the L-lysine salts of glutarate, pimelate, suberate, azelate, sebacate, formate, acetate, propionate, butyrate and hydrogen malate.

Canadian Pat. No. 1,209,037 describes a medicament comprising the product of the reaction of a $C_1$ to $C_6$ carboxylic acid on a basic amino acid. The authors describe a medicament containing arginine butyrate or lysine butyrate together with interferon and/or an immunostimulant agent.

SUMMARY

In a first aspect, the present invention includes a food product, comprising L-lysine butyrate. The food product does not contain gluten and is not a baked product.

In a second aspect, the present invention includes an oral dosage form comprising 25 mg to 5.0 g L-lysine butyrate. The oral dosage form is a tablet, a capsule, or a sealed packet containing powder.

In a third aspect, the present invention includes a method of supplementing butyrate in a person, comprising orally administering L-lysine butyrate to the person to provide at least one of the following: a $C_{max}$, a $t_{1/2}$, or an AUC equal to or greater than a $C_{max}$, a $t_{1/2}$, or an AUC determined in Example 4 for 25 mg to 5 g of L-lysine butyrate; a $C_{max}$, a $t_{1/2}$, or an AUC equal to or greater than a $C_{max}$, a $t_{1/2}$, or an AUC determined in Example 4 for 25 mg to 5 g of L-lysine butyrate normalized by the amount of L-lysine butyrate administered, or a $C_{max}$, a $t_{1/2}$, or an AUC equal to or greater than a $C_{max}$, a $t_{1/2}$, or an AUC determined in Example 4 for 25 mg to 5 g of L-lysine butyrate normalized by the butyric acid molar equivalent amount administered.

In a fourth aspect, the present invention includes a method of providing a nootropic effect to a person, comprising supplementing butyrate in the person.

In a fifth aspect, the present invention includes a method of treating a condition, comprising supplementing butyrate in the person. The person is a patient in need thereof, and the amount of L-lysine butyrate administered is an amount effect to treat the condition. The condition is at least one selected from the group consisting of solid tumor cancers, malignancies, hematological diseases, blood dyscrasias, epilepsy, metabolic diseases, type 2 diabetes, cardiovascular diseases, cardiac diseases, inflammatory diseases, arthritis, gut dysbiosis, constipation, diarrhea, leaky gut syndrome, Crohn's disease, inflammatory bowel disease, obesity, ulcerative colitis, drug addiction, alcoholism, depression, anxiety, Alzheimer's disease, pain and Parkinson's Disease.

In a sixth aspect, the present invention includes a method of losing weight, improving cognition, inducing or maintaining ketosis, or improving athletic performance, the method comprising supplementing butyrate in the person.

In a seventh aspect, the present invention includes a method of treating or mitigating mild-to-moderate pain, the method comprising supplementing butyrate in the person.

Definitions

"Short-chain fatty acid" (SCFA) means a carboxylic acid with an aliphatic chain of two to six carbon atoms, which is either saturated or unsaturated. Examples include R—C(O)OH, where R is ethyl, propyl, or butyl, preferably n-propyl or $CH_3(CH_2)2$-. Examples also include butyric acid, also referred to as butanoic acid, and 1-propanecarboxylic acid.

L-lysine butyrate is a compound having a chemical formula containing butyrate anion, $CH_3(CH_2)2(C=O)O^-$ and L-lysine cation, $^+(NH_3)(CH_2)4C(NH_2)(C=O)OH$, in a 1:1 molar ratio.

"Treating a tumor" or "treating a cancer" means to significantly inhibit growth and/or metastasis of the tumor or cancer. Growth inhibition can be indicated by reduced tumor volume or reduced occurrences of metastasis. Tumor growth can be determined, for example, by examining the tumor volume via routine procedures (such as obtaining two-dimensional measurements with a dial caliper). Metastasis can be determined by inspecting for tumor cells in secondary sites or examining the metastatic potential of biopsied tumor cells in vitro.

$C_{max}$, also referred to as peak concentration, is a pharmacokinetic measure used to determine dosing. As used in the present application, $C_{max}$ is the highest concentration of butyrate in the blood after dosing. As used in the present application, $t_{1/2}$, or half-life, is the time from administration until the concentration of butyrate in blood is at 50% of $C_{max}$.

AUC, or Area Under the Curve, is a measure of overall drug exposure. As used in the present application, AUC refers to the area under the curve for the concentration of butyrate in blood, from the time of administration until the concentration of butyrate reaches the same level or below that found in the blood prior to administration, or is at such a low level that it cannot be detected.

The terms "dietary ingredient", "dietary supplement" and "food additive" have the meanings as set forth in U.S. Government regulations.

The amounts, percentages and ratios of compositions described herein are all by weight, unless otherwise stated.

DETAILED DESCRIPTION

Compounds currently identified as useful for butyrate administration, including butyric acid, sodium butyrate and tributyrin, suffer from several disadvantages. Butyric acid is a foul smelling and unpalatable tasting liquid, making it difficult to handle, store, and measure, as well as difficult to administer orally in significant amounts, or to provide a ready-to-mix powder formulation. Butyric acid plasma clearance is very rapid: when given intravenously, its half-life is only about six minutes (Egorin et al., 1999; A. A. Miller et al., 1987; S. J. Miller, 2004; Newmark & Young, 1995).

Sodium butyrate is a crystalline solid. However, sodium butyrate is over 20% sodium, making its use as a butyrate supplement contraindicated in persons with high blood pressure, or those persons following a low-sodium diet. Furthermore, studies performed using large amounts of sodium butyrate given continuously or with multiple daily doses intravenously or by intraperitoneal infusion, clearly show that plasma levels achieved are largely under the minimal concentration desired or required to produce the same desired pharmacodynamic effects obtained in vitro (J. S. Chen et al., 2003; Serpe et al., 2004). These studies suggest that sodium butyrate has a very short half-life by any route of administration. Furthermore, if sodium butyrate comes into contact with even a trace of moisture, it emits a faint odor of butyric acid. Potassium, magnesium, calcium and zinc butyrates suffer from problems similar to sodium butyrate.

Butyric acid esters, notably tributyrin, are also well known to possess poor taste and smell. Additionally, tributyrin is a liquid at room temperature, adding to the difficulty in storage, transport, and administration. While the half-life of tributyrin is longer than that of butyric acid and sodium butyrate, the absorption kinetics of tributyrin require very large oral doses to reach therapeutic plasma levels ($C_{max}$), which makes effective dosing difficult due to the poor taste and smell. Additional information regarding the oral and parenteral pharmacokinetics of butyric acid, tributyrin, and metallic ionic salts of butyric acid (for example, sodium butyrate) can be found in the literature (Conley et al., 1998; Edelman et al., 2003; Kantharaj & Jayaraman, 2011; Kuefer et al., 2007; Newmark et al., 1994).

Attempts to mechanically produce acceptable solid or powdered products of butyric acid or tributyrin with better organoleptic properties (taste and smell) have been largely unsuccessful. While it is possible to spray dry or agglomerate butyric acid or tributyrin to various substances (for example, prebiotic fibers such as acacia gum, inulin, guar gum or even carbohydrates such as maltodextrin) and indeed such products have been made and commercialized, there are still serious and significant limitations. First, these types of products typically contain only 40%-60% of active ingredient by weight, so an even larger dose is required. Second, the poor organoleptic properties of butyric acid and tributyrin still have not yet been adequately masked by agglomeration or spray drying. Thus, while a fine dry powder can be produced, the poor taste and smell characteristics are not ameliorated significantly by spray drying or agglomeration. Finally, the impact on bioavailability and pharmacokinetics has not been demonstrated to be significantly improved by merely spray drying or agglomerating butyric acid or tributyrin onto a fiber or carbohydrate-based agent.

After extensive testing and experimentation, it has been determined that L-lysine butyrate provides an excellent source for administration of butyrate to a person or non-human animal. L-lysine butyrate has been determined to have physical and organoleptic properties which make it easy to handle and use, in particular, it does not have an unpleasant odor or taste to humans, it is a solid that is stable to storage at room temperature, it is not hygroscopic and does not hydrolyze in air. It may be formed into a free-flowing powder and may be mixed with other powder ingredients commonly used in ready-to-mix powder formulations which may be mixed with water or another aqueous beverage to prepare a ready-to-drink composition. Since it does not have an unpleasant odor or taste, it is possible to prepare products containing large amounts L-lysine butyrate, for example 1 g, 2 g or 5 g per serving, which are palatable, unlike butyric acid and tributyrin, or with acceptable amounts of sodium, unlike sodium butyrate. L-lysine butyrate allows for oral administration in amounts much greater than other sources of butyrate, providing for a higher $C_{max}$, $t_{1/2}$ and greater AUC of butyrate in absolute value, as compared to other common butyrate supplements. The lack of an unpleasant odor also allows for topical and transdermal administration.

L-lysine butyrate may be used in the formulation of dietary supplements, nutritional products, infant formulas, functional foods, and/or functional beverages, for example, as solid dose formulations such as gummies, tablets, troches, caplets, lozenges, or capsules or as flavored, powdered products for reconstitution and solvation in water or other aqueous solutions. The butyric acid amino acid salt disclosed herein may also be used in the formulation of drugs or pharmacological agents, for example, as solid dose formulations such as tablets, troches, caplets, lozenges, or capsules or as flavored, powdered products for reconstitution and solvation in water or other aqueous solutions. Also possible are creams, lotions and ointments for transdermal and topical administration.

Oral administration of L-lysine butyrate may preferably be in an amount of 25 mg, 50 mg, 100 mg, 150 mg, 250 mg, 300 mg, at least 500 mg, more than 500 mg, at least 600 mg, 700 mg, 750 mg, 800 mg, 1000 mg (or 1 g), 1.25 g, 1.5 g, 2 g, 2.5 g, 3 g, 4 g, 4.5 g, or at most 5 g, including values and ranges therebetween. Such dosages may be administered once or twice per day, or even more often. Administration by other routes, such as by injection or infusion, may be in an amount of 25 mg, 50 mg, 100 mg, 150 mg, 250 mg, 300 mg, 500 mg, greater than 500 mg, 600 mg, 750 mg, 1 g, 2 g, 3 g, 4 g, 5 g, 10 g, 20 g, or even 50 g. Such an injection or infusion may be carried out once or twice per day, or even more often. Other routes of administration, such as through an enema, are also possible. All the proceeding dosage amounts may be by weight of the L-lysine butyrate contained in the product, or may be L-lysine butyrate in an amount on a molar basis equivalent to the stated weight amount, but of butyric acid.

A single oral administration of 5 g to a person has been shown to produce undesirable mental effects, interfering with focus and alertness, similar to intoxication, but such effects are acceptable if appropriate precautions are taken in advance. A single oral administration of 2 g to a person has been shown to produce pleasant mental effects, including an improvement in focus, alertness, concentration, reduction in anxiety, and a general feeling of well-being. A small dosage of 25 mg or 50 mg, is effective to calm a baby. A single oral administration above 5 g to a large non-human animal may be appropriate, for example horses, camels, bovines, other farm animals, and dogs.

L-lysine butyrate also has an excellent $C_{max}$, $t_{1/2}$ and AUC, as compared to equivalent molar amounts of butyric acid, sodium butyrate, and tributyrin, for oral administration, and similar results are expected for other routes of administration, such as by injection or by enema. Preferably, the $C_{max}$, $t_{1/2}$ and AUC achieved in a person, or an average value achieved in a plurality of persons, by oral administration, is at least that achieved by oral administration of 25 mg, 50 mg, 100 mg, 250 mg, 500 mg, 1 g, 2 g or 5 g of L-lysine butyrate, by the protocol shown in Example 4, or values therebetween. Alternatively, preferably the $C_{max}$, $t_{1/2}$ and AUC achieved in a person, or an average value achieved in a plurality of persons, by oral administration, is that achieved by oral administration of 25 mg, 50 mg, 100 mg, 250 mg, 500 mg, 1 g, 2 g or 5 g of L-lysine butyrate, by the protocol shown in Example 4, normalized by the amount administered (that is, on a per gram administered basis), or values therebetween. Alternatively, preferably the $C_{max}$, $t_{1/2}$ and AUC achieved in a person, or an average value achieved in a plurality of persons, by oral administration, is that achieved by oral administration of 25 mg, 50 mg, 100 mg, 250 mg, 500 mg, 1 g, 2 g or 5 g of butyric acid equivalent molar amount of L-lysine butyrate, by the protocol shown in Example 4, or values therebetween.

A pharmaceutical composition is formulated to be compatible with its intended route of administration, including intravenous, intradermal, subcutaneous, intramuscular, transdermal and oral. Solutions and suspensions used for parenteral, intradermal, intramuscular or subcutaneous application, and creams, lotions and ointments for transdermal and topical administration, can include a sterile diluent, such as water for injection, saline solution, Ringer's solutions, dextrose solution, polyethylene glycols, glycerin, propylene glycol or other synthetic solvents; antibacterial agents such as benzyl alcohol or methyl parabens; antioxidants such as ascorbic acid or sodium bisulfite; buffers such as acetates, citrates or phosphates, and agents for the adjustment of tonicity such as sodium chloride or dextrose. The pH can be adjusted with acids or bases, such as hydrochloric acid or sodium hydroxide. Pharmaceutical compositions for injection are sterile, and pharmaceutical compositions for oral administration are preferably sterile. Pharmaceutical compositions preferably contain a pharmaceutically acceptable carrier, includes any and all solvents, dispersion media, coatings, antibacterial and antifungal agents, isotonic and absorption delaying agents which are compatible with pharmaceutical administration. A pharmaceutically acceptable carrier includes any and all solvents, dispersion media, coatings, antibacterial and antifungal agents, isotonic and absorption delaying agents which are compatible with pharmaceutical administration (see, for example, Remington Education: Pharmaceutics (Pharmaceutical Press) ISBN 9780857110701, Published 1 Jun. 2014). Non-pharmaceutical compositions or formulations are orally administered, and may contain any agent acceptable for pharmaceutical compositions, as well as any agent or additive used in food. Non-pharmaceutical compositions are typically not sterile.

Various disease states may be treated, prevented or improved by administration of L-lysine butyrate, and include solid tumor cancers or malignancies, hematological or blood dyscrasias, epilepsy, metabolic disease including type 2 diabetes, cardiovascular disease, cardiac disease, inflammatory disease states including arthritis, gut dysbiosis, constipation, diarrhea, leaky gut syndrome, Crohn's disease, inflammatory bowel disease, obesity, ulcerative colitis, drug addiction, alcoholism, depression, anxiety, Alzheimer's disease, and/or Parkinson's Disease. Analgesic effects, including the eliminating minor-to-moderate pain and discomfort, were observed after oral administration of L-lysine butyrate. Some of the disease states which may treated are those previously known to be treated with butyric acid or sodium butyrate.

Pharmaceutical and non-pharmaceutical formulations may be pre-packaged in ready-to-administer form, in amounts that correspond with a single dosage, appropriate for a single administration, referred to as a unit dosage form. Unit dosage forms for injection can be enclosed in ampoules, disposable syringes or vials made of glass or plastic. Unit dosage forms for oral administration include tablets, capsules, package powder, ready-to-mix beverage powders, or ready-to-drink liquid formulations, that are premeasured to provide the desired unit dosage for a single administration. Multi-dosage forms are a set of unit dosage forms package together, such as a bottle of tablets or capsules, or a box of unit dosage forms of a ready-to-mix powder beverage in sealed packets.

Oral dosage forms include tablets, capsules, L-lysine butyrate powder, ready-to-mix powder formulations, and ready-to-drink liquid formulations. Such oral dosage forms may include pharmaceutically acceptable excipients in the tablets, capsules, and pre-measured L-lysine butyrate powder, such as one or more flow agents; suitable carriers for use in tablet and capsule compositions or formulations include inert organic and inert inorganic carrier materials such as gelatin, starch, magnesium stearate, talc, gums, silicon dioxide, stearic acid, and cellulose (see, for example, Remington Education: Pharmaceutics (Pharmaceutical Press) ISBN 9780857110701, Published 1 Jun. 2014). When in the form of a pre-measured L-lysine butyrate powder, ready-to-mix powder formulations, and ready-to-drink liquid formulations, the forms may include one or more flavoring agents, one or more sweetening agents, one or more food coloring agents, one or more flow agents, one or more thickening agents, and/or any other food safe additive. Other consumable forms or food product forms, such a chocolate bars, cereals, gummies, lollipops, candies, lozenges, hard candies, chocolates, nut butters, ice cream, popsicles, yogurts, cottage cheese, powder coffee creamers, powdered waffle and pancakes mixes, protein powders, protein and nutritional drinks, hydration and electrolyte drinks and drink mixes, are also possible. Also possible are dietary ingredients, dietary supplements and food additives, which preferably contain flavorings and/or sweeteners. Preferably, the food product does not contain wheat or flour, or is not made using flour, or does not contain gluten. Preferably, the food product is not a baked good. In addition, L-lysine butyrate powder may be added to any existing ready-to-mix powder formulation, to produce a new oral dosage form.

Gummies (also referred to as gummy candies, including various types of gummy vitamins and supplements), often share a set of core ingredients that give them their characteristic chewy texture and sweetness. In addition to L-lysine butyrate, such a gummy may include gelling agent (such as gelatin, pectin, and agar-agar), a sweetener (such as sugar, glucose syrup, corn syrup and fructose, which may also help control texture), flavorings (such as citric acid, malic acid, fruit flavors, fruit juices, vegetable juices, natural flavorings and artificial flavorings), colorings (such as natural colorings, fruit juices, vegetable juices, artificial colorings) and water. These ingredients are mixed, heated, and poured into molds to set. Depending on the type of gummy, additional ingredients like vitamins, minerals, or other functional ingredients might be included, in addition to the L-lysine butyrate.

Non-pharmaceutical forms, which are not sterile, may also include probiotic bacteria, and/or spores of probiotic bacteria. Probiotic bacteria include bacteria of the species *Lactobacillus, Bifidobacterium, Saccharomyces, Streptococcus, Enterococcus, Escherichia*, and *Bacillus* (Probiotics Fact Sheet for Health Professionals, National Institutes of Health, Office of Dietary Supplements (Nov. 3, 2023), available at ods.od.nih.gov/factsheets/Probiotics-HealthProfessional). Because L-lysine butyrate is not hygroscopic, formulation which contain probiotic bacteria and/or spores of probiotic bacteria, are storage stable. Preferably, the non-pharmaceutical forms and the pharmaceutical forms are storage stable in air for at least one, two, three, four, five, six, twelve, eighteen, or twenty-four months.

Probiotic bacteria include *Akkermansia muciniphila, Anaerostipes caccae, Bifidobacterium adolescentis, Bifidobacterium bifidum, Bifidobacterium infantis, Bifidobacterium longum, Bifidobacterium lactis, Bifidobacterium breve, Butyrivibrio fibrisolvens, Clostridium acetobutylicum, Clostridium aminophilum, Clostridium beijerinckii, Clostridium butyricum, Clostridium colinum, Clostridium coccoides, Clostridium indolis, Clostridium nexile, Clostridium orbiscindens, Clostridium propionicum, Clostridium xylanolyticum, Enterococcus faecium, Eubacterium hallii, Eubacterium rectale, Fibrobacter succinogenes, Oscillospira guilliermondii, Roseburia cecicola, Roseburia inulinivorans, Ruminococcus jlavefaciens, Ruminococcus gnavus, Ruminococcus obeum, Stenotrophomonas nitritireducens, Streptococcus cremoris, Streptococcus faecium, Streptococcus infantis, Streptococcus mutans, Streptococcus thermophilus, Anaerofustis stercorihominis, Anaerostipes hadrus, Anaerotruncus colihominis, Clostridium sporogenes, Clostridium tetani, Coprococcus, Coprococcus eutactus, Eubacterium cylindroides, Eubacterium dolichum, Eubacterium ventriosum, Roseburia faeccis, Roseburia hominis, Roseburia intestinalis, Lactobacillus bifidus, Lactobacillus acidophilus, Lactobacillus bulgaricus, Lactobacillus rhamnosus, Lactobacillus casei, Lactobacillus salivarius, Lactobacillus plantarum, Lactobacillus coagulans, Acidaminococcus fermentans, Acidaminococcus intestine, Blautia hydrogenotrophica, Citrobacter amalonaticus, Citrobacter freundii, Clostridium aminobutyricum Clostridium bartlettii, Clostridium cochlearium, Clostridium kluyveri, Clostridium limosum, Clostridium malenominatum, Clostridium pasteurianum, Clostridium peptidivorans, Clostridium saccharobutylicum, Clostridium sporosphaeroides, Clostridium sticklandii, Clostridium subterminale, Clostridium symbiosum, Clostridium tetanomorphum, Eubacterium oxidoreducens, Eubacterium pyruvativorans, Eubacterium limosum, Methanobrevibacter smithii, Morganella morganii, Peptoniphilus asaccharolyticus, Peptostreptococcus, Faecalibacterium praustnitzii, Butyrivibrio fibrisolvens*, and *Fusobacterium nucleatum*.

Excipients which may be included in formulations may be one or more of antioxidants, preservatives, flavoring agents, coloring agents, sweetening agents, chelating agents, cosolvents, humectants, buffering agents, pH adjusting agents, dispersion agents, suspending aids, flow agents, and emulsifying agents (see, for example, Remington Education: Pharmaceutics (Pharmaceutical Press) ISBN 9780857110701, Published 1 Jun. 2014). Nutritional supplements, including proteins, vitamins, minerals, soluble and/or insoluble fiber, may also be included in the formulations. Preferably, the excipients are considered "Generally Regarded As Safe (GRAS).

Other ingredients which may be present in the formulation include one or more of prebiotics, short-chain fatty acids, medium-chain triglycerides, botanicals, amino acids and other dietary ingredients.

Prebiotics include complex carbohydrates, complex sugars, resistant dextrins, resistant starch, amino acids, peptides, nutritional compounds, biotin, polydextrose, fructooligosaccharides (FOS), galactooligosaccharides (GOS), inulin, starch, lignin, *psyllium*, chitin, chitosan, gums, guar gum, high amylose cornstarch (HAS), cellulose, -glucans, hemicelluloses, lactulose, mannooligosaccharides, mannan oligosaccharides (MOS), oligofructose-enriched inulin, oligofructose, oligodextrose, tagatose, trans-galactooligosaccharide, pectin, xylooligosaccharides (XOS), locust bean gum, P-glucan, methylcellulose, chicory root inulin, apple pectin, maltodextrin, and agave inulin. Short-chain fatty acids include acetic acid, monoacetin, diacetin, triacetin, propionic acid, monopropionin, dipropionin, tripropionin, valeric acid, monovalerin, divalerin, trivalerin and isovaleric acid. Medium-chain triglycerides are triglycerides with two or three fatty acids having an aliphatic tail of 6-12 carbon atoms; examples include triglycerides of caproic acid, caprylic acid, capric acid and lauric acid.

Botanicals include ginger root powder and extract, green tea powder and extract, butterbur powder and extract, feverfew powder and extract, milk thistle powder and extract, licorice root powder and extract, *astragalus* root powder and extract, eleuthero root powder and extract, ashwagandha powder and extract, fenugreek seed powder and extract, marshmallow root powder and extract, turmeric root powder and extract, toothed club moss powder and extract, American *ginseng* powder and extract, *Panax ginseng* powder and extract, *Rhodiola rosea* powder and extract, *alpina* galanga powder and extract, sage powder and extract, amla fruit powder and extract, and grains of paradise powder and extract.

Vitamins include thiamine variations and derivatives, riboflavin variations and derivatives, niacin variations and derivatives, pantothenic acid variations and derivatives, pyridoxine variations and derivatives, folic acid variations and derivatives, vitamin B12 variations and derivatives, biotin variations and derivatives, vitamin C variations and derivatives, vitamin D variations and derivatives, vitamin E variations and derivatives, vitamin K variations and derivatives, and choline variations and derivatives. Minerals include sodium, potassium, phosphorus, chloride, calcium, magnesium, zinc, iron, iodine, selenium, copper, manganese, chromium, molybdenum and boron. Amino acids include alanine, proline, threonine, leucine, glycine, aspartic acid, isoleucine, valine, glutamine, asparagine, serine, lysine, histidine, tryptophan, tyrosine, phenylalanine, glutamic acid, arginine, cysteine, taurine, citrulline, and ornithine.

Others dietary ingredients include superoxide dismutase, n-acetyl cysteine, glutathione, coenzyme Q10, pyrroloquinoline quinone (PQQ), caffeine, theacrine, methylliberine, liberine, paraxanthine, theobromine, theophylline, 1-theanine, GABA, luteolin, fisetin, apigenin, spermidine, spermine, 1-ergothioneine, 1-carnitine variations, acetyl-l-carnitine, alpha lipoic acid variations and derivatives, betaine variations, creatine variations, beta-alanine, alpha-glycerylphosphorylcholine variations and derivatives, I-β-aminoisobutyric acid, berberine, dihydroberberine, glycerol, cytidine-5'-diphosphocholine variations and derivatives, lactoferrin, and astaxanthin.

Flavorings (or flavoring agents) include manzanate (apple), diacetyl, acetylpropionyl, acetoin (buttery), isoamyl acetate (banana), benzaldehyde (bitter almond, cherry), cinnamaldehyde (cinnamon), ethyl propionate (fruity), methyl anthranilate (grape), limonene (orange), ethyl decadienoate (pear), allyl hexanoate (pineapple), ethyl maltol (sugar, cotton candy), 2,4-dithiapentane (truffle), ethylvanillin (vanilla), methyl salicylate (wintergreen), fruit juices and vegetable juices. Colorings (or coloring agents) include annatto, caramel coloring, carmine, elderberry juice, lycopene, paprika, turmeric/curcumin, betanin, anthocyanin, beta-carotene, indigo carmine, allura red AC, quinoline yellow WS, brilliant blue FCF, indigotine, fast green FCF, erythrosine, tartrazine and sunset yellow FCF, fruit juices and vegetable juices. Sweeteners (or sweetening agents) include sugar, honey, molasses, corn syrup, high-fructose corn syrup, aspartame, acesulfame potassium, sucralose, neotame, advantame and saccharin.

Exemplary formulations include:

Formulation 1: A powdered, dietary supplement containing 25 mg to 2000 mg of L-lysine butyrate, 0.5 g to 8.0 g of inulin, flavoring agent(s) q.s. to taste, and sweetening agent(s) q.s. to taste. This composition can be mixed into four to sixteen ounces of water or other suitable aqueous based liquid and consumed orally.

Formulation 2: A powdered, dietary supplement containing 25 mg to 2000 mg of L-lysine butyrate, 0.5 g to 5.0 g of water-soluble acacia fiber (gum arabic), flavoring agent(s) q.s. to taste, and sweetening agent(s) q.s. to taste. This composition can be mixed into four to sixteen ounces of water or other suitable aqueous based liquid and consumed orally.

Formulation 3: A powdered, dietary supplement containing 25 mg to 2000 mg of L-lysine butyrate, one billion to ten billion colony forming units (CFU) one or more strains of probiotic bacteria or bacterial spores from the genus *Lactobacillus*, flavoring agent(s) q.s. to taste, and sweetening agent(s) q.s. to taste. This composition can be mixed into four to sixteen ounces of water or other suitable aqueous based liquid and consumed.

Formulation 4: A powdered, dietary supplement containing 25 mg to 2000 mg of L-lysine butyrate, one billion to five billion colony forming units (CFU) of one or more strains of probiotic bacteria or bacterial spores from the genus *Bifidobacterium*, flavoring agent(s) q.s. to taste, and sweetening agent(s) q.s. to taste. This composition can be mixed into four to sixteen ounces of water or other suitable aqueous based liquid and consumed orally.

Formulation 5: A powdered, dietary supplement containing 25 mg to 2000 mg of L-lysine butyrate, one billion to two billion colony forming units (CFU) of one or more strains of probiotic bacteria or bacterial spores from the genus *Bacillus*, flavoring agent(s) q.s. to taste, and sweetening agent(s) q.s. to taste. This composition can be mixed into four to sixteen ounces of water or other suitable aqueous based liquid and consumed orally.

Formulation 6: a solid dose, dietary supplement including gelatin capsules each containing 25 mg to 1000 mg of L-lysine butyrate and a silicate-based flow agent to assist with encapsulation q.s. This composition can be consumed orally, one to three capsules per administration.

Formulation 7: a solid dose, dietary supplement including gelatin capsules each containing 25 mg to 1000 mg of L-lysine butyrate, one million to one billion colony forming units (CFU) of one or more strains of probiotic bacteria or bacterial spores from the genus *Lactobacillus* and a silicate-based flow agent to assist with encapsulation q.s. This composition can be consumed orally, one to three capsules per administration.

Formulation 8: a solid dose, dietary supplement including gelatin capsules each containing 25 mg to 1000 mg of L-lysine butyrate, one million to one billion colony forming units (CFU) of one or more strains of probiotic bacteria or bacterial spores from the genus *Bifidobacterium*, and a silicate-based flow agent to assist with encapsulation q.s. This composition can be consumed orally, one to three capsules per administration.

Formulation 9: a solid dose, dietary supplement including gelatin capsules each containing 25 mg to 1000 mg of L-lysine butyrate, one million to five hundred million colony forming units (CFU) of one or more strains of probiotic bacteria or bacterial spores from the genus *Bacillus*, and a silicate-based flow agent to assist with encapsulation q.s. This composition can be consumed orally, one to three capsules per administration.

Formulation 10: A powdered, dietary supplement including 25 mg to 5000 mg of L-lysine butyrate, flavoring agent(s) q.s. to taste, and sweetening agent(s) q.s. to taste. This composition can be mixed into four to twenty ounces of water or other suitable aqueous based liquid and consumed orally.

Formulation 11: A powdered, baby formula containing 25 mg to 200 mg of L-lysine butyrate and 7.0 g to 9.0 g of Similac® Advance Powdered Baby Formula (Abbott). This composition can be mixed into four to eight ounces of water or other suitable aqueous based liquid and consumed.

Formulation 12: A powdered, baby formula containing 25 mg to 200 mg of L-lysine butyrate and 7.0 g to 9.0 g of Enfamil® Neuro Pro Powdered Baby Formula (Mead Johnson & Company LLC). This composition can be mixed into four to eight ounces of water or other suitable aqueous based liquid and consumed.

Formulation 13: A powdered, baby formula containing 25 mg to 200 mg of L-lysine butyrate and 7.0 g to 9.0 g of Nutramigen® with Probiotic LGG® Hypoallergenic Infant Formula (Mead Johnson & Company LLC). This composition can be mixed into four to eight ounces of water or other suitable aqueous based liquid and consumed.

Formulation 14: A powdered, protein drink mix containing 100 mg to 2000 mg of L-lysine butyrate and 25 g to 35 g of RYSE™ Loaded Protein Powder. Any flavor may be used, including Skippy Peanut flavor and Giant Tito Cheese Cake flavor. This composition can be mixed into six to twelve ounces of water or other suitable aqueous based liquid and consumed.

Formulation 15: A powdered, protein drink mix containing 100 mg to 2000 mg of L-lysine butyrate and 15 g to 25 g of Vital Proteins® Collagen Peptides Powder. This composition can be mixed into six to twelve ounces of water or other suitable aqueous based liquid and consumed.

Formulation 16: A powdered, dietary supplement mix containing 100 mg to 500 mg of L-lysine butyrate and 6 g to 8 g of Pedialyte® Powder (Abbott). This composition can be mixed into sixteen ounces of water or other suitable aqueous based liquid and consumed.

Formulation 17: A powdered, dietary supplement containing 100 mg to 2000 mg of L-lysine butyrate and 6 g to 8 g of Gundry MD MCT Wellness Powder. This composition can be mixed into eight to twelve ounces of water or other suitable aqueous based liquid and consumed.

Formulation 18: A beverage, containing 100 mg to 2000 mg of L-lysine butyrate and 4 oz to 8 oz of orange juice. This composition is ready to drink.

Formulation 19: A beverage, containing 100 mg to 2000 mg of L-lysine butyrate and 6 oz to 10 oz Gatorade™. This composition is ready to drink.

Formulation 20: A chewable gummy, containing 100 mg to 500 mg L-lysine butyrate, tapioca syrup, cane sugar, apple pectin, citric acid, natural flavors, and medium chain triglycerides.

EXAMPLES

Example 1: Preparation of L-Lysine Butyrate and L-Arginine Butyrate

An attempt was made to produce various butyrates using a drop titration method. Using a 10 ml borosilicate glass burette with a glass stopcock, ~0.3 ml of butyric acid was added dropwise per minute into a borosilicate glass petri dish each containing 10 g of the amino acids or amino acid derivatives (cations) listed in Table 1. In all instances, there was no observable reaction or salt formation. Analytical laboratory testing using nuclear magnetic resonance (1H-NMR) confirmed that no ionic salt was formed between butyric acid and any of the ten amino acids or amino acid derivatives by this method.

Next, an attempt was made to produce the various butyrates by dissolving equimolar amounts of the putative cations and butyric acid in a solvent. The ten amino acids or amino acid derivatives (putative cations) listed in Table 1 were dissolved in the solvent with an equimolar amount of butyric acid, allow to react for 24 hours at room temperature. Following centrifugation at 1000 RPM for 30 minutes, the solvent was removed and any precipitate (in the form of a cake) was collected and weighed. Using a 50/50 (w/w) co-solvent mixture of cyclohex-1-ene (CAS No 110-83-8) and ethanol (CAS No 64-17-5) both L-arginine butyrate and L-lysine butyrate were successfully synthesized, with respective yields of 86.2% and 66.6%. The composition of both salts was confirmed using 1H-NMR.

Using methyl tert-butyl ether (MTBE, 2-methoxy-2-methylpropane, CAS No 1634-04-4) as the sole solvent, both L-arginine butyrate and L-lysine butyrate were synthesized, with respective yields of 97.2% and 96.4%. The composition of both salts was confirmed using 1H-NMR. Additionally, a citrulline butyrate salt also appeared to be formed using this method, but attempts to precipitate or otherwise obtain the salt from the solution were not successful. However, MTBE has a highly unpleasant scent and taste, reminiscent of turpentine, and it was determined that any product formed using MTBE would have an unacceptable taste and smell. (MTBE is readily detectable by humans in concentrations as low as parts per billion).

Using ethanol (CAS No 64-17-5) as the sole solvent, both L-arginine butyrate and L-lysine butyrate were synthesized, with respective yields of 91.2% and 90.5%. Both salts were confirmed using 1H-NMR.

The L-arginine butyrate prepared using ethanol as the sole solvent was a white to off-white powder. It had virtually no detectable scent and had a very neutral taste. However, the L-arginine butyrate was quite hygroscopic. An L-arginine butyrate sample left exposed at room temperature to air rapidly pulled water from the atmosphere, which transformed the powder from a white to off-white/pale gold color, and formed hard, rock-like clumps, readily visible after only 24 hours. After seven (7) days of exposure, the sample of L-arginine butyrate had significantly hydrated into, large solid masses with a substantial, visible color change to a light gold or tan color.

The L-lysine butyrate prepared using ethanol as the sole solvent was a light, pale yellow to yellow powder. It had a mild and not unpleasant scent vaguely reminiscent of cheddar cheese, and a slightly sweet and pleasant taste. An L-lysine butyrate sample remained a fine, free-flowing yellow powder after 24 hours of exposure at room temperature to air. After seven (7) days of exposure at room temperature to air, L-lysine butyrate remained a fine, free-flowing powder with no color change. Further testing confirmed that L-lysine butyrate remained a fine, free-flowing powder after thirty (30) days of exposure at room temperature to air.

TABLE 1

Attempted preparation of salts of amino acids and amino acid derivatives of butyric acid.

| Putative Cation | Anion | Product formed and isolated? |
|---|---|---|
| Creatine | Butyric Acid | No |
| Betaine | Butyric Acid | No |
| L-Leucine | Butyric Acid | No |
| Glutamine | Butyric Acid | No |
| Taurine | Butyric Acid | No |
| Glycine | Butyric Acid | No |
| Citrulline | Butyric Acid | No |
| L-Arginine | Butyric Acid | Yes |
| L-Lysine | Butyric Acid | Yes |
| Beta-Alanine | Butyric Acid | No |

An L-lysine butyrate sample was subject to further analytical chemical analyses, including ASTM D7588 FT-IR spectroscopy; melting point analysis; and examination by visible microscopy. The FT-IR spectra was similar to, and consistent with, L-lysine and butyric acid spectra, and when compared to the FR-IR spectra of L-lysine monohydrate, it was determined that the L-lysine butyrate sample was anhydrous. The L-lysine butyrate was determined to be water: methanol soluble, and formed a solid mass. The melting point was determined to be about 200° C.

The synthesis of L-lysine butyrate was scaled up to produce about one kilogram of product using ethanol as the sole solvent. The method used is shown below:

(1) 600.0 g of L-lysine was added to a 20-liter glass reactor.
(2) 10 liters of ethanol was then added to the reactor.
(3) The above was stirred for two hour at 20-30° C. to allow the L-lysine to dissolve.
(4) 361.6 g n-butyric acid was then added to the glass reactor.
(5) The above was stirred for two hours at 20-30° C. to allow for complete dissolution.
(6) The resultant mixture was centrifugated at 1000 RPM for one hour to isolate a solid, "wet cake" precipitate.
(7) The "wet cake" product was allowed to dry at 45° C. for 24 h and formed a fine, free flowing light yellow powder. 934.7 g of fine, free flowing yellow powder (97.2% of theoretical yield) was ultimately recovered. The powder was tested by 1H-NMR and determined to be L-lysine butyrate.

Example 2: Study to Assess the Organoleptic Properties of L-Lysine Butyrate

A study was conducted to assess the organoleptic properties of L-lysine butyrate compared to other butyrate supplement products. This study was single-blinded and consisted of ten (10) study subjects (eight male subjects, two female subjects, average age=33.8 years). Study subjects were asked to assess the smell and taste of a 200 mg sample of each of the following: tributyrin (Sigma Aldrich), sodium butyrate (Sigma Aldrich), butyric acid (Sigma Aldrich), L-lysine butyrate (from Example 1), CoreBiome® (tributyrin agglomerated to acacia fiber, 55% tributyrin net content) (Compound Solutions, Inc.) and 30% butyric acid agglomerated onto 70% maltodextrin (Spray-Tek, LLC). Study subjects were given a 200 mm anchored visual analog scale, with the low end being "very bad", followed by "bad", "neutral", "good" and the high end being "very good". The labelling of the visual analog scale for both smell and taste were the same. A value between 1 and 200 was then assigned for each study subjects rating of each of the taste and the smell of each tested material, based on the position marked by the study subject on the visual analog scale. The study results are presented in Tables 2-5.

TABLE 2

Taste assessment

| Age (Y) | Sex | Tributyrin | Sodium Butyrate | Butyric Acid | L-Lysine Butyrate | Corebiome ® Tributyrin | 30% Butyric acid agglomerated to 70% maltodextrin |
|---|---|---|---|---|---|---|---|
| 24 | M | 3 | 4 | 1 | 102 | 6 | 7 |
| 42 | F | 3 | 4 | 0 | 100 | 2 | 2 |
| 27 | M | 3 | 6 | 1 | 103 | 5 | 3 |
| 23 | M | 5 | 3 | 2 | 100 | 6 | 4 |
| 41 | M | 3 | 3 | 1 | 93 | 12 | 2 |
| 36 | M | 2 | 5 | 2 | 100 | 6 | 6 |
| 28 | F | 4 | 4 | 0 | 100 | 3 | 2 |
| 34 | M | 3 | 0 | 0 | 102 | 4 | 3 |
| 30 | M | 4 | 0 | 0 | 107 | 2 | 3 |
| 53 | M | 3 | 6 | 0 | 108 | 5 | 6 |

TABLE 3

Statistical analysis-taste

| Butyrate supplement products | Mean | N | Std. Dev. | Median | Min | Max |
|---|---|---|---|---|---|---|
| Tributyrin | 3.30 | 10 | .823 | 3.00 | 2 | 5 |
| Sodium Butyrate | 3.50 | 10 | 2.121 | 4.00 | 0 | 6 |
| Butyric Acid | 0.70 | 10 | .823 | 0.50 | 0 | 2 |
| L-Lysine Butyrate | 101.50 | 10 | 4.170 | 101.00 | 93 | 108 |
| CoreBiome ® | 5.10 | 10 | 2.885 | 5 | 2 | 12 |
| Butyric Acid Malto | 3.80 | 10 | 1.874 | 3 | 2 | 7 |

TABLE 4

Smell assessment

| Age (Y) | Sex | Tributyrin | Sodium Butyrate | Butyric Acid | L-Lysine Butyrate | Corebiome ® Tributyrin | 30% Butyric acid agglomerated to 70% maltodextrin |
|---|---|---|---|---|---|---|---|
| 24 | M | 3 | 12 | 2 | 109 | 16 | 12 |
| 42 | F | 2 | 5 | 0 | 101 | 36 | 26 |
| 27 | M | 2 | 6 | 0 | 98 | 50 | 45 |
| 23 | M | 3 | 14 | 1 | 115 | 50 | 40 |
| 41 | M | 5 | 44 | 2 | 103 | 44 | 40 |
| 36 | M | 4 | 38 | 3 | 102 | 70 | 56 |
| 28 | F | 3 | 21 | 0 | 100 | 53 | 50 |
| 34 | M | 3 | 4 | 0 | 100 | 45 | 44 |
| 30 | M | 3 | 27 | 0 | 114 | 21 | 26 |
| 53 | M | 2 | 3 | 0 | 109 | 14 | 20 |

TABLE 5

Statistical analysis-smell

| Butyrate supplement products | Mean | N | Std. Dev. | Median | Min | Max |
|---|---|---|---|---|---|---|
| Tributyrin | 3.00 | 10 | 0.943 | 3.00 | 2 | 5 |
| Sodium Butyrate | 17.40 | 10 | 14.714 | 13.00 | 3 | 44 |
| Butyric Acid | 0.80 | 10 | 1.135 | 0.00 | 0 | 3 |
| L-Lysine Butyrate | 105.10 | 10 | 6.154 | 102.5 | 98 | 115 |
| CoreBiome ® | 39.90 | 10 | 18.071 | 44.50 | 14 | 70 |
| Butyric Acid Malto | 35.90 | 10 | 14.161 | 40.00 | 12 | 56 |

Example 3: Study to Assess Nootropic and Related Properties of L-Lysine Butyrate In another experiment, L-lysine butyrate in a dose range of 500 mg to 5,000 mg was administered as an aqueous solution to six individuals aged between 22 and 55 years, comprising two women and four men. All participants reported feeling more relaxed, less tired, more sociable, and able to concentrate on tasks more effectively within thirty minutes of administration. The observed effects were dose-dependent, with larger doses of L-lysine butyrate providing greater effects and longer duration, lasting up to four hours.

In another experiment, L-lysine butyrate in a dose of 2 g, and on a separate occasion 5 g, was administered in encapsulated form, to 2 individuals. A further individual was administered L-lysine butyrate in a dose of 2 g in encapsuled form. A single oral administration of 2 g produced pleasant mental effects, including an improvement in focus, alertness, concentration, reduction in anxiety, and a general feeling of well-being. Two of the individuals also indicate the 2 g administration provided an analgesic effect, eliminating minor-to-moderate pain and discomfort. A single oral administration of 5 g produced undesirable mental effects, interfering with focus and alertness, with effects similar to intoxication.

Example 4: Study to Assess Pharmacokinetic Properties of L-Lysine Butyrate

This study is a randomized, three-arm, interventional study of N=10 apparently healthy men between 25 and 45 years old to be recruited at a single investigational center. This study will quantify plasma butyrate pharmacokinetic responses to a single equimolar dose of three different butyrate products. Participants will attend four study visits. During Visit 1, participants will be screened for participation (medical history, routine blood work, and background baseline diet). During Visits 2, 3, and 4 participants will ingest equimolar doses of either sodium butyrate, lysine butyrate or CoreBIOME®. Plasma samples will be obtained from an indwelling catheter prior to product administration (time 0) as well as 20-, 45-, 90-, 150- and 210-minutes post-dose to quantify plasma butyrate pharmacokinetic responses. Comprehensive adverse event monitoring will take place throughout the study. The study is designed and set up for execution in compliance with ICH-GCP guidelines to ensure subject safety and the scientific integrity of the data.

Outcome Variables:

Primary variable: plasma butyrate levels prior to product administration (time 0), as well as 20-, 45-, 90-, 150-, and 210-minutes post-dose.

Secondary variables: Visual analog scales for mood and cognitive function (well-being, nausea, indigestion, focus).

Tertiary variables: Safety and tolerability as determined by vital signs and side effect profile/adverse events monitoring throughout the study.

Design: Randomized, single-blind, three-arm, crossover, interventional clinical trial.

Subjects: Ten (N=10) healthy men between the ages of 25 and 45. All participants will be screened using health history questionnaires, vital signs, and blood testing.

Inclusion Criteria:
  (i) Provide voluntary signed and dated informed consent.
  (ii) Be in good health as determined by medical history and routine blood chemistries.
  (iii) Age between the ages of 25 and 45 (inclusive).

(iv) Body Mass Index of 18.5-24.9 (inclusive).
(v) Body weight of at least 110 pounds.
(vi) Normotensive (seated, resting systolic blood pressure 21 140 mm Hg and diastolic blood pressure ≤90 mm Hg. If the first measurement is slightly elevated above these limits, the subject will be given a brief (5-minute) rest period, and two more measurements will be taken. The average of all three measurements will be used to determine eligibility).
(vii) Normal seated, resting heart rate (<90 per minute).
(viii) Willing to duplicate their previous 24-hour diet, refrain from alcohol, caffeine, and exercise for 24 hours and fast for 10 hours prior to each of the treatments.
(ix) Participant agrees to maintain existing dietary and physical activity patterns throughout the study period.
(x) Participant is willing and able to comply with the study protocol.

Exclusion Criteria:
(i) A history of unstable or new-onset cardiovascular/ cardiorespiratory, liver, or renal disease.
(ii) The participant's alcohol consumption is more than two standard alcoholic drinks per day or more than 10 drinks per week or has a history of drug/alcohol abuse or dependence.
(iii) History of diabetes (any form) or any endocrine disorder.
(iv) Fasting blood sugar of >125 mg/dL.
(v) Current smokers or smoking cessation within the past month (28 days).
(vi) History of hyperparathyroidism or an untreated thyroid disease.
(vii) History of malignancy in the previous five years except for non-melanoma skin cancer (basal cell cancer or squamous cell cancer of the skin).
(viii) Any history of gastrointestinal bypass surgery, etc., or any known functional gastrointestinal disorder that may impact nutrient absorption, e.g., short bowel syndrome, atrophic gastritis, IBD, diarrheal illnesses, history of colon resection, gastroparesis, gastric resection, celiac disease, or Inherited Errors of Metabolism (such as PKU).
(ix) Chronic inflammatory condition or disease (e.g., rheumatoid arthritis, Crohn's Disease, ulcerative colitis, lupus, HIV/AIDS, etc.).
(x) History of using butyrate or tributyrin-containing dietary supplements within the past seven days.
(xi) Known allergy or sensitivity to any ingredient in the test formulations as listed on the product label.
(xii) Any other diseases or conditions that, in the opinion of the medical staff, could confound the primary endpoints or place the subject at increased risk of harm if they were to participate.

Diet: At screening, all participants will complete a 24-hour diet recall. To maintain standardization for the duration of the study, participants will be asked to maintain their current energy and macronutrient intake (maintain their current diet without changing how or what they eat). To characterize the study subjects, each participant's diet (via standardized, validated 24-hour diet record method) will be captured and analyzed via Nutritionix to determine energy (total kcals) and macronutrient (carbohydrate, fat and protein) content. To replicate baseline-testing conditions as closely as possible, prior to each visit to the laboratory, participants will follow their previously recorded 24-hour diet records (i.e., be asked to eat the same foods prior to and fast for 10 hours prior to testing).

Bloodwork/Testing: At screening, a single blood draw of 12 mL will be performed for routine screening: Complete Blood Count (CBC), Comprehensive Metabolic Panel (CMP), and Lipid Panel will be performed. On the morning of the $2^{nd}$, $3^{rd}$, and 4th visits, and after an overnight fast (10 hours), an intravenous catheter (flexible tubing to enable blood sampling) will be inserted into their arm by a study nurse. Blood samples (6 mL) will be collected up to 6 times over 3.5 hours. At Visit 2, Visit 3, and Visit 4, blood samples will be obtained at 0 minutes (baseline) prior to the administration of the study product, then at 20 minutes, 45 minutes, 90 minutes, 150 minutes, and 210 minutes following ingestion of the study product. The total volume of blood drawn for this study (all visits) is approximately 120 mL. For comparison, the standard blood donation is approximately 480 mL (two cups). In case of a laboratory error in processing, backup blood samples will be retained from each time point (Visits 2, 3, and 4).

Exercise and Physical Activity Control: Throughout the study, and to standardize the participants, all will be asked to maintain their activities of daily living and abstain from heavy exercise and physical activity for 48 hours prior to each visit.

Intervention/Test Products: After qualifying for the study, participants will receive each of the following treatments in a randomized order:
(i) Sodium butyrate (3 capsules delivering 786 mg of butyric acid equivalent)
(ii) L-lysine butyrate (3 capsules delivering 786 mg of butyric acid equivalent)
(iii) CoreBIOME® (3 capsules delivering 786 mg of butyric acid equivalent)

Interventions will be provided in generic, identical-looking, coded capsules. Participants will orally ingest three capsules with 8 oz of water after catheter placement. Visits 2 and 3 will be seven days apart, and visits 3 and 4 will be seven days apart.

Analysis: Values will be determined for $C_{max}$, $t_{1/2}$ and AUC in each study participant, and an average value achieved in all study participants, for each product tested. $C_{max}$, $t_{1/2}$ and AUC will be determined for 500 mg, 1 g, 2 g or 5 g of L-lysine butyrate, normalized by the amount of L-lysine butyrate administered (that is, on a per gram administered basis), as well as values normalized by the butyric acid equivalent amount administered.

REFERENCES

Bartolomaeus, H., Balogh, A., Yakoub, M., Homann, S., Markó, L., Hōges, S., Tsvetkov, D., Krannich, A., Wundersitz, S., Avery, E. G., Haase, N., Kräker, K., Hering, L., Maase, M., Kusche-Vihrog, K., Grandoch, M., Fielitz, J., Kempa, S., Gollasch, M., . . . Wilck, N. (2019). Short-Chain Fatty Acid Propionate Protects From Hypertensive Cardiovascular Damage. *Circulation* (New York, N.Y.), 139(11), 1407-1421.

Bourassa, M. W., Alim, I., Bultman, S. J., & Ratan, R. R. (2016). Butyrate, neuroepigenetics and the gut microbiome: Can a high fiber diet improve brain health?*Neuroscience Letters*, 625, 56-63.

Byrne, C. S., Chambers, E. S., Morrison, D. J., & Frost, G. (2015). The role of short chain fatty acids in appetite regulation and energy homeostasis. International Journal of *Obesity*, 39(9), 1331-1338.

Canfora, E. E., Jocken, J. W., & Blaak, E. E. (2015). Short-chain fatty acids in control of body weight and insulin sensitivity. *Nature Reviews. Endocrinology*, 11(10), 577-591.

Chen, J. S., Faller, D. V., & Spanjaard, R. A. (2003). Short-Chain Fatty Acid Inhibitors of Histone Deacetylases: Promising Anticancer Therapeutics?*Current Cancer Drug Targets*, 3(3), 219-236.

Conley, B. A., Egorin, M. J., Tait, N., Rosen, D. M., Sausville, E. A., Dover, G., Fram, R. J., & Van Echo, D. A. (1998). Phase I study of the orally administered butyrate prodrug, tributyrin, in patients with solid tumors. *Clinical Cancer Research*, 4(3), 629-634.

Edelman, M. J., Bauer, K., Khanwani, S., Tait, N., Trepel, J., Karp, J., Nemieboka, N., Eun-Joo, C., & Echo, D. V. (2003). Clinical and pharmacologic study of tributyrin: An oral butyrate prodrug. *Cancer Chemotherapy and Pharmacology*, 51(5), 439-444.

Egorin, M. J., Yuan, Z.-M., Sentz, D. L., Plaisance, K., & Eiseman, J. L. (1999). Plasma pharmacokinetics of butyrate after intravenous administration of sodium butyrate or oral administration of tributyrin or sodium butyrate to mice and rats. *Cancer Chemotherapy and Pharmacology*, 43(6), 445-453.

Faller, D. V., Ghosh, S., Feldman, T., Lerner, A., Smith, J., Goy, A., Berenson, R., & Perrine, S. (2009). Short-Term Exposure to Arginine Butyrate, in Combination with Ganciclovir, Is as Effective as Continuous Exposure for Virus-Targeted Therapy of EBV-Positive Lymphomas. *Blood*, 114(22), 4754.

Guerron, A. D., Rawat, R., Sali, A., Spurney, C. F., Pistilli, E., Cha, H.-J., Pandey, G. S., Gernapudi, R., Francia, D., Farajian, V., Escolar, D. M., Bossi, L., Becker, M., Zerr, P., Porte, S. de la, Gordish-Dressman, H., Partridge, T., Hoffman, E. P., & Nagaraju, K. (2010). Functional and Molecular Effects of Arginine Butyrate and Prednisone on Muscle and Heart in the mdx Mouse Model of Duchenne Muscular Dystrophy. *PLOS ONE*, 5(6), e11220.

Hamer, H. M., Jonkers, D. M. A. E., Bast, A., Vanhoutvin, S. A. L. W., Fischer, M. A. J. G., Kodde, A., Troost, F. J., Venema, K., & Brummer, R.-J. M. (2009). Butyrate modulates oxidative stress in the colonic mucosa of healthy humans. *Clinical Nutrition*, 28(1), 88-93.

Kantharaj, E., & Jayaraman, R. (2011). Histone deacetylase inhibitors as therapeutic agents for cancer therapy: Drug metabolism and pharmacokinetic properties. In *Drug Development—A Case Study Based Insight into Modern Strategies*. IntechOpen. doi.org/10.5772/27799.

Kaye, D. M., Shihata, W. A., Jama, H. A., Tsyganov, K., Ziemann, M., Kiriazis, H., Horlock, D., Vijay, A., Giam, B., Vinh, A., Johnson, C., Fiedler, A., Donner, D., Snelson, M., Coughlan, M. T., Phillips, S., Du, X.-J., EI-Osta, A., Drummond, G., . . . Marques, F. Z. (2020). Deficiency of Prebiotic Fiber and Insufficient Signaling Through Gut Metabolite-Sensing Receptors Leads to Cardiovascular Disease. *Circulation* (New York, N. Y.), 141(17), 1393-1403.

Kim, S., Goel, R., Kumar, A., Qi, Y., Lobaton, G., Hosaka, K., Mohammed, M., Handberg, E. M., Richards, E. M., Pepine, C. J., & Raizada, M. K. (2018). Imbalance of gut microbiome and intestinal epithelial barrier dysfunction in patients with high blood pressure. *Clinical Science* (London, England.: 1979), 132(6), 701-718.

Kuefer, R., Genze, F., Zugmaier, W., Hautmann, R. E., Rinnab, L., Gschwend, J. E., Angelmeier, M., Estrada, A., & Buechele, B. (2007). Antagonistic Effects of Sodium Butyrate and N-(4-Hydroxyphenyl)-retinamide on Prostate Cancer. *Neoplasia*, 9(3), 246-253.

Kuksis, A. (2000). Biochemistry of glycerolipids and formation of chylomicrons. *Fat Digestion and Absorption*., 119-181.

Lupton, J. R. (2004). Microbial Degradation Products Influence Colon Cancer Risk: The Butyrate Controversy. *The Journal of Nutrition*, 134(2), 479-482.

Marques, F. Z., Nelson, E., Chu, P.-Y., Horlock, D., Fiedler, A., Ziemann, M., Tan, J. K., Kuruppu, S., Rajapakse, N. W., EI-Osta, A., Mackay, C. R., & Kaye, D. M. (2017). High-Fiber Diet and Acetate Supplementation Change the Gut Microbiota and Prevent the Development of Hypertension and Heart Failure in Hypertensive Mice. *Circulation* (New York, N.Y.), 135(10), 964-977.

McGovern, M. M., Wasserstein, M. P., Aron, A., & Perrine, S. P. (2003). Biochemical effect of intravenous arginine butyrate in x-linked adrenoleukodystrophy. *The Journal of Pediatrics*, 142(6), 709-713.

McMahon, L., Tamary, H., Askin, M., Adams-Graves, P., Eberhardt, R. T., Sutton, M., Wright, E. C., Castaneda, S. A., Faller, D. V., & Perrine, S. P. (2010). A randomized phase II trial of Arginine Butyrate with standard local therapy in refractory sickle cell leg ulcers. *British Journal of Haematology*, 151(5), 516-524.

Merchak, A., & Gaultier, A. (2020). Microbial metabolites and immune regulation: New targets for major depressive disorder. *Brain, Behavior, & Immunity—Health*, 9, 100169.

Miller, A. A., Kurschel, E., Osieka, R., & Schmidt, C. G. (1987). Clinical pharmacology of sodium butyrate in patients with acute leukemia. *European Journal of Cancer and Clinical Oncology*, 23(9), 1283-1287.

Miller, S. J. (2004). Cellular and physiological effects of short-chain fatty acids. *Mini Reviews in Medicinal Chemistry*, 4(8), 839-845.

Morrison, D. J., & Preston, T. (2016). Formation of short chain fatty acids by the gut microbiota and their impact on human metabolism. *Gut Microbes*, 7(3), 189-200.

Moss, G. P., Smith, P. a. S., & Tavernier, D. (1995). Glossary of class names of organic compounds and reactivity intermediates based on structure (IUPAC Recommendations 1995). *Pure and Applied Chemistry*, 67(8-9), 1307-1375.

Mueller, N. T., Zhang, M., Juraschek, S. P., Miller, E. R., & Appel, L. J. (2020). Effects of high-fiber diets enriched with carbohydrate, protein, or unsaturated fat on circulating short chain fatty acids: Results from the OmniHeart randomized trial. *The American Journal of Clinical Nutrition*, 111(3), 545-554.

Newmark, H. L., Lupton, J. R., & Young, C. W. (1994). Butyrate as a differentiating agent: Pharmacokinetics, analogues and current status. *Cancer Letters*, 78(1), 1-5.

Newmark, H. L., & Young, C. W. (1995). Butyrate and phenylacetate as differentiating agents: Practical problems and opportunities. *Journal of Cellular Biochemistry*, 59(S22), 247-253.

Offermanns, S., Colletti, S. L., Lovenberg, T. W., Semple, G., Wise, A., & IJzerman, A. P. (2011). International Union of Basic and Clinical Pharmacology. LXXXII: Nomenclature and Classification of Hydroxy-carboxylic Acid Receptors (GPR81, GPR109A, and GPR109B). *Pharmacological Reviews*, 63(2), 269-290.

Perrine, S. P., Hermine, O., Small, T., Suarez, F., O'Reilly, R., Boulad, F., Fingeroth, J., Askin, M., Levy, A., Mentzer, S. J., Di Nicola, M., Gianni, A. M., Klein, C., Horwitz, S., & Faller, D. V. (2006). A phase 1/2 trial of arginine butyrate and ganciclovir in patients with Epstein-Barr virus-associated lymphoid malignancies. *Blood*, 109 (6), 2571-2578.

Pizzorno, J. E., Murray, M. T., & Joiner-Bey, H. (2016). Inflammatory Bowel Syndrome. In *The Clinician's handbook of natural medicine E-book* (pp. 547-564). Elsevier Health Sciences.

Rhys-Jones, D., Climie, R. E., Gill, P. A., Jama, H. A., Head, G. A., Gibson, P. R., Kaye, D. M., Muir, J. G., & Marques, F. Z. (2021). Microbial Interventions to Control and Reduce Blood Pressure in Australia (MICRoBIA): Rationale and design of a double-blinded randomised crossover placebo controlled trial. *Trials*, 22(1), 1-7.

Scheppach, W., Sommer, H., Kirchner, T., Paganelli, G.-M., Bartram, P., Christl, S., Richter, F., Dusel, G., & Kasper, H. (1992). Effect of butyrate enemas on the colonic mucosa in distal ulcerative colitis. *Gastroenterology*, 103 (1), 51-56.

Seedorf, H., Fricke, W. F., Veith, B., BrOggemann, H., Liesegang, H., Strittmatter, A., Miethke, M., Buckel, W., Hinderberger, J., Li, F., Hagemeier, C., Thauer, R. K., & Gottschalk, G. (2008). Genome of *Clostridium kluyveri*, a strict anaerobe with unique metabolic features. *Proceedings of the National Academy of Sciences—PNAS*, 105(6), 2128-2133.

Serpe, L., Laurora, S., Pizzimenti, S., Ugazio, E., Ponti, R., Canaparo, R., Briatore, F., Barrera, G., Gasco, M. R., Bernengo, M. G., Eandi, M., & Zara, G. P. (2004). Cholesteryl butyrate solid lipid nanoparticles as a butyric acid pro-drug: Effects on cell proliferation, cell-cycle distribution and c-myc expression in human leukemic cells. *Anti—Cancer Drugs*, 15(5), 525-536.

Sher, G. D., Ginder, G. D., Little, J., Yang, S., Dover, G. J., & Olivieri, N. F. (1995). Extended Therapy with Intravenous Arginine Butyrate in Patients with β-Hemoglobinopathies. *New England Journal of Medicine*, 332(24), 1606-1610.

Urbano, A., Koc, Y., & Foss, F. M. (1998). Arginine butyrate downregulates p210 bcr-abl expression and induces apoptosis in chronic myelogenous leukemia cells. *Leukemia*, 12(6), 930-936.

Wong, J. M. W., de Souza, R., Kendall, C. W. C., Emam, A., & Jenkins, D. J. A. (2006). Colonic Health: Fermentation and Short Chain Fatty Acids. *Journal of Clinical Gastroenterology*, 40(3), 235.

Probiotics Fact Sheet for Health Professionals, National Institutes of Health, Office of Dietary Supplements (Nov. 3, 2023), available at ods.od.nih.gov/factsheets/Probiotics-HealthProfessional.

U.S. Pat. No. 3,024,272.
U.S. Pat. No. 3,015,567.
Canadian Pat. No. 1,209,037.

What is claimed is:

1. A food product, comprising:
   L-lysine butyrate,
   a flavoring agent, and
   a sweetening agent,
   wherein the food product is a ready-to-mix powder formulation, a ready-to-drink liquid formulation or a gummy,
   the L-lysine butyrate is present in an amount of 25 m to 5 g, and
   the food product does not contain gluten and is not a baked product.

2. The food product of claim 1, wherein the food product is the ready-to-mix powder formulation or the ready-to-drink liquid formulation selected from the group consisting of infant formula, protein supplements, hydration drinks and electrolyte drinks.

3. The food product of claim 1, further comprising a probiotic bacteria or bacterial spores selected from the group consisting of *Lactobacillus, Bifidobacterium, Saccharomyces, Streptococcus, Enterococcus, Escherichia, Bacillus*, and mixtures thereof, and
   wherein the food product is the ready-to-mix powder formulation.

4. The food product of claim 1, wherein the L-lysine butyrate is present in an amount of 500 mg to 2 g.

5. An oral dosage form comprising: 25 mg to 5.0 g L-lysine butyrate, wherein the oral dosage form is a tablet, a capsule, or a sealed packet containing powder and the oral dosage does not contain gluten and is not a baked product.

6. The oral dosage form of claim 5, further comprising a flow agent.

7. The oral dosage form of claim 5, wherein the oral dosage form is a unit dosage form comprising:
   0.5 g, 1 g or 2 g of L-lysine butyrate, or
   L-lysine butyrate in an amount on a molar basis equivalent to 0.5 g, 1 g or 2 g butyric acid.

8. The oral dosage form of claim 5, further comprising a probiotic bacteria or bacterial spores selected from the group consisting of *Lactobacillus, Bifidobacterium, Saccharomyces, Streptococcus, Enterococcus, Escherichia, Bacillus*, and mixtures thereof.

9. The oral dosage form of claim 5, further comprising at least one nutritional supplement selected from the group consisting of prebiotics, short-chain fatty acids, medium-chain triglycerides, botanicals and amino acids.

10. A method of supplementing butyrate in a person, comprising orally administering the food product of claim 1 to the person.

11. The method of claim 10, further comprising:
    preparing a beverage from the ready-to-mix powder formulation, by mixing the ready-to-mix powder with water or an aqueous liquid;
    wherein the orally administering comprises the person drinking the beverage.

12. The method of claim 10, wherein the food product contains 0.5 g to 2 g of the L-lysine butyrate.

13. A method of providing a nootropic effect to a person, comprising supplementing butyrate in the person by the method of claim 10.

14. The method of claim 13, wherein the nootropic effect provided is at least one effect selected from the group consisting of the person becoming, within 30 minutes of administration: more relaxed, less tired, more sociable, calm and able to concentrate on tasks more effectively.

15. A method of treating a condition, comprising supplementing butyrate in the person by the method of claim 10, wherein:
    the person is a patient in need thereof,
    the amount of L-lysine butyrate administered is an amount effect to treat the condition, and
    the condition is at least one selected from the group consisting of solid tumor cancers, malignancies, hematological diseases, blood dyscrasias, epilepsy, metabolic diseases, type 2 diabetes, cardiovascular diseases, cardiac diseases, inflammatory diseases, arthritis, gut dysbiosis, constipation, diarrhea, leaky gut syndrome, Crohn's disease, inflammatory bowel disease, obesity, ulcerative colitis, drug addiction, alcoholism, depression, anxiety, Alzheimer's disease, pain and Parkinson's Disease.

16. A method of losing weight, improving cognition, inducing or maintaining ketosis, or improving athletic performance, the method comprising supplementing butyrate in the person by the method of claim 10.

17. A method of treating or mitigating mild-to-moderate pain, the method comprising supplementing butyrate in the person by the method of claim 10.

18. A method of supplementing butyrate in a person, comprising orally administering the oral dosage form of claim 5 to the person.

19. The method of claim 18, wherein the oral dosage form comprises 0.5 g to 2 g of the L-lysine butyrate.

20. A method of providing a nootropic effect to a person, comprising supplementing butyrate in the person by the method of claim 18.

21. The method of claim 20, wherein the nootropic effect provided is at least one effect selected from the group consisting of the person becoming, within 30 minutes of administration: more relaxed, less tired, more sociable, calm and able to concentrate on tasks more effectively.

22. A method of treating a condition, comprising supplementing butyrate in the person by the method of claim 18, wherein:

the person is a patient in need thereof, the amount of L-lysine butyrate administered is an amount effect to treat the condition, and the condition is at least one selected from the group consisting of solid tumor cancers, malignancies, hematological diseases, blood dyscrasias, epilepsy, metabolic diseases, type 2 diabetes, cardiovascular diseases, cardiac diseases, inflammatory diseases, arthritis, gut dysbiosis, constipation, diarrhea, leaky gut syndrome, Crohn's disease, inflammatory bowel disease, obesity, ulcerative colitis, drug addiction, alcoholism, depression, anxiety, Alzheimer's disease, pain and Parkinson's Disease.

23. A method of losing weight, improving cognition, inducing or maintaining ketosis, or improving athletic performance, the method comprising supplementing butyrate in the person by the method of claim 18.

24. A method of treating or mitigating mild-to-moderate pain, the method comprising supplementing butyrate in the person by the method of claim 18.

\* \* \* \* \*

UNITED STATES PATENT AND TRADEMARK OFFICE
CERTIFICATE OF CORRECTION

| | | |
|---|---|---|
| PATENT NO. | : 12,226,383 B1 | Page 1 of 1 |
| APPLICATION NO. | : 18/651454 | |
| DATED | : February 18, 2025 | |
| INVENTOR(S) | : Kneller et al. | |

It is certified that error appears in the above-identified patent and that said Letters Patent is hereby corrected as shown below:

In the Claims

Column 21, Line 62, please delete "25 m" and insert --25 mg--

Column 24, Line 3, please delete "effect" and insert --effective--

Signed and Sealed this
Eighth Day of April, 2025

Coke Morgan Stewart
*Acting Director of the United States Patent and Trademark Office*